(12) United States Patent
Cha

(10) Patent No.: US 9,540,679 B2
(45) Date of Patent: Jan. 10, 2017

(54) HELICAL WRAPPING OF SINGLE-WALLED CARBON NANOTUBES BY GENOMIC DNA

(75) Inventor: Jennifer Nam Cha, Union City, CA (US)

(73) Assignee: International Business Machines Corporation, Armonk, NY (US)

( * ) Notice: Subject to any disclaimer, the term of this patent is extended or adjusted under 35 U.S.C. 154(b) by 1816 days.

(21) Appl. No.: 12/573,905

(22) Filed: Oct. 6, 2009

(65) Prior Publication Data

US 2010/0173142 A1    Jul. 8, 2010

Related U.S. Application Data

(62) Division of application No. 11/313,098, filed on Dec. 20, 2005, now Pat. No. 7,625,702.

(51) Int. Cl.
| | |
|---|---|
| *C12M 1/00* | (2006.01) |
| *C12M 1/34* | (2006.01) |
| *C12Q 1/68* | (2006.01) |
| *C07H 21/02* | (2006.01) |
| *B32B 9/00* | (2006.01) |

(52) U.S. Cl.
CPC .......... *C12Q 1/6806* (2013.01); *Y10S 977/734* (2013.01); *Y10S 977/742* (2013.01); *Y10S 977/746* (2013.01); *Y10T 428/249924* (2015.04); *Y10T 428/2918* (2015.01)

(58) Field of Classification Search
CPC .............. C12M 1/00; C12M 1/34; C12Q 1/68; Y10S 977/742; B32B 9/00
USPC ......... 435/6.1, 283.1, 287.2; 536/23.1, 24.3; 977/742; 428/292.1, 367

See application file for complete search history.

(56) References Cited

U.S. PATENT DOCUMENTS

| | | | |
|---|---|---|---|
| 5,830,655 A | 11/1998 | Monforte et al. | |
| 6,656,693 B2 * | 12/2003 | Saraf et al. | 435/6.11 |
| 7,498,423 B2 | 3/2009 | Zheng et al. | |
| 2002/0172963 A1 | 11/2002 | Kelley et al. | |
| 2003/0134267 A1 | 7/2003 | Kang et al. | |
| 2004/0063100 A1 | 4/2004 | Wang | |
| 2004/0126802 A1 | 7/2004 | Brubaker | |
| 2004/0132072 A1 | 7/2004 | Zheng et al. | |
| 2004/0248144 A1 | 12/2004 | Mir | |
| 2005/0009039 A1 | 1/2005 | Jagota et al. | |

OTHER PUBLICATIONS

Dovbesko et al, Study of DNA interaction with carbon nanotubes, Semiconductor physics, Quantum Electronics & optoelectronics, 2003, 6, 105-108.*

Dovbeshko-2 et al, Surface enhanced IR absorption of nuclei cacids from tumor cells: FITR reflectance study, Biopolymers (Biospectroscopy), 2002, 67, 470-486.*
Notice of Allowance (Mail Date Jul. 17, 2009) for U.S. Appl. No. 11/313,098, filed Dec. 20, 2005; First Named Inventor Cha et al.
Xin et al., DNA-Templated Nanotube Localization; JACS 2003, 125; pp. 8710-8711.
Zheng et al., Structure-Based Carbon Nanotube Sorting by Sequence-Dependent DNA Assembly; 2003 Science 302; pp. 1545-1548.
Nakashima et al., DNA Dissolves Single-walled Carbon Nanotubes in Water; 2003 Chemistry Letters vol. 32, No. 5; pp. 456-457.
Dwyer et al., DNA-functionalized single-walled carbon nanotubes; 2002, Nanotechnology 13; pp. 601-604.
Barhoumi, Aoune, Semi-Biosynthesis of DNA Nanostructures, Marshall University thesis, Mary 2004; pp. 1-123.
Katz et al., Biomolecule-functionalized carbon nanotubes: applications in nanobioelectronics; Institute of Chemistry, The Hebrew University of Jerusalem, Jerusalem, Israel; Chemphyschem. Aug. 20, 2004; 5(8):1084-104.
Bae et al.; Electrochemical fabrication of single-walled carbon nanotubes-DNA complexes by poly(ethylenedioxythiophene) and photocurrent generation by excitation of an intercalated chromophore; Department of Chemistry and Biochemistry, Graduate School of Engineering, Kyushu University, Fukuoka 812-8581, Japan; Org Biomol Chem. Apr. 21, 2004; 2(8):1139-44. Epub Mar. 18, 2004.
Keren et al.; DNA-Templated Carbon Nanotube Field-Effect Transistor; Science, vol. 302; 21 Nov. 2003; pp. 1380-1381; www.sciencemag.org.
Lay et al.; Simple Route to Large-Scale Ordered Arrays of Liquid-Deposited Carbon Nanotubes; 2004 American Chemical Society; Nano Letters 2004, vol. 4, No. 4; pp. 603-606; Published on Web Mar. 13, 2004.
Miller et al.; Large-scale assembly of carbon nanotubes; 2003 Nature Publishing Group, vol. 425; Sep. 4, 2003; pp. 36-37; www.nature.com/nature.
Zheng et al.; DNA-assisted dispersion and separation of carbon nanotubes; 2003 Nature Publishing Group, vol. 2; May 2003; pp. 338-342; www.nature.com/naturematerials.

* cited by examiner

*Primary Examiner* — Narayan Bhat
(74) *Attorney, Agent, or Firm* — Schmeiser, Olsen & Watts

(57) ABSTRACT

A structure and method for forming single-stranded DNA segments/single-wall carbon nanotube complexes and a method of preparing single-stranded DNA segments. The method for forming single-stranded DNA segments/single-wall carbon nanotube complexes including: attaching single-stranded DNA segments to single-wall carbon nanotubes to form single-stranded DNA segment/single-wall carbon nanotube complexes, each of the single-stranded DNA segments having a same length of greater than 2,000 bases.

20 Claims, 5 Drawing Sheets

HELICAL WRAPPING OF SINGLE-WALLED CARBON NANOTUBES BY GENOMIC DNA

This application is a division of U.S. patent application Ser. No. 11/313,098 filed on Dec. 20, 2005, now U.S. Pat. No. 7,625,702, issued Dec. 1, 2009.

FIELD OF THE INVENTION

The present invention relates to the field of forming carbon nanotube/DNA complexes. More specifically, the present invention relates to a method of forming single-stranded DNA molecules suitable for dispersing single-wall carbon nanotubes, a method of forming a single-wall carbon nanotube/single-stranded DNA complex, and a structure of a single-wall carbon nanotube/single-stranded DNA complex.

BACKGROUND OF THE INVENTION

Due to their nanometer sizes and molecular recognition capabilities, biological systems have garnered much attention as vehicles for the directed assembly of nanoscale materials. One of the largest challenges of this research has been to successfully interface biological systems with nanoscale materials, such as carbon nanotubes. To this end methods utilizing short DNA oligomers that can disperse single-wall carbon nanotubes in water have been developed. However, the need for specific repeating base sequences limits use of this method. Therefore, there is a need for DNA based methods to disperse single-wall carbon nanotubes without the limitations of specific repeating base sequences.

SUMMARY OF THE INVENTION

A first aspect of the present invention is a method, comprising: attaching single-stranded DNA segments to single-wall carbon nanotubes to form single-stranded DNA segment/single-wall carbon nanotube complexes, each of the single-stranded DNA segments having a length of greater than 2,000 bases.

A second aspect of the present invention is a method, comprising: replicating double-stranded DNA segments in a polymerase chain reaction in the presence of a first primer and a second primer, the second primer having a terminating thiol group attached to one end of the second primer, each replicated double-stranded DNA segment having first and second complementary strands, the second strand having a thiol group at one end of the second strand; attaching metal nanoparticles to the thiol groups of the replicated double-stranded DNA segments; breaking the replicated double-stranded DNA segments into complementary first and second single-stranded DNA segments, the second single-stranded DNA segments including the thiol groups and metal nanoparticles; and removing the first single-stranded DNA segments from the second single-stranded DNA segments.

A third aspect of the present invention is a structure, comprising: a single-wall carbon nanotube; and a single-stranded DNA segment helically wound around the single-wall carbon nanotube, the single-stranded DNA segment being greater than 2,000 bases in length.

BRIEF DESCRIPTION OF DRAWINGS

The features of the invention are set forth in the appended claims. The invention itself, however, will be best understood by reference to the following detailed description of an illustrative embodiment when read in conjunction with the accompanying drawings, wherein:

DETAILED DESCRIPTION OF THE INVENTION

Carbon nanotubes (CNTs) are closed-cage molecules composed of $sp^2$-hybridized carbon atoms arranged in hexagons and pentagons. Carbon nanotubes may be single-wall nanotubes (SWNT) which are hollow tube like structures or multi-walled nanotubes (MWNT) which resemble sets of concentric cylinders. For the purposes of the present invention, the terms carbon nanotube (CNT) and is single-wall nanotube (SWNT) are defined single-wall carbon nanotubes. The SWNTs of the present invention may be doped with elements other than carbon, examples of which include, but are not limited to phosphorus, arsenic, boron and metals.

SWNTs may be made by any number of methods known in the art and are commercially available. In one example, SWNTs are made using high pressure carbon monoxide process (HiPCo) process (P. Nikolaev et al. *Chem. Phys. Lett.* 313, 91-97 (1999)).

In the interest of using DNA as a dispersion and patterning vehicle for SWNTs for use in microelectronics, the ideal linearly extended length of the DNA should be in the order of several microns. DNA length may also be expressed as the number of base pairs (bp) attached to the phosphate backbone of the DNA molecule. The DNA utilized by the present invention is genomic DNA. Though coliphage lambda DNA was used in the experimental portions of the present invention, the invention is not limited to being practiced with lambda DNA and any genomic DNA may be used. Lambda DNA was chosen because its entire 48,502 base pair sequence is known and its restriction enzyme map fully characterized. Lambda DNA is derived from *E. coli* and is commercially available.

Figure 1:
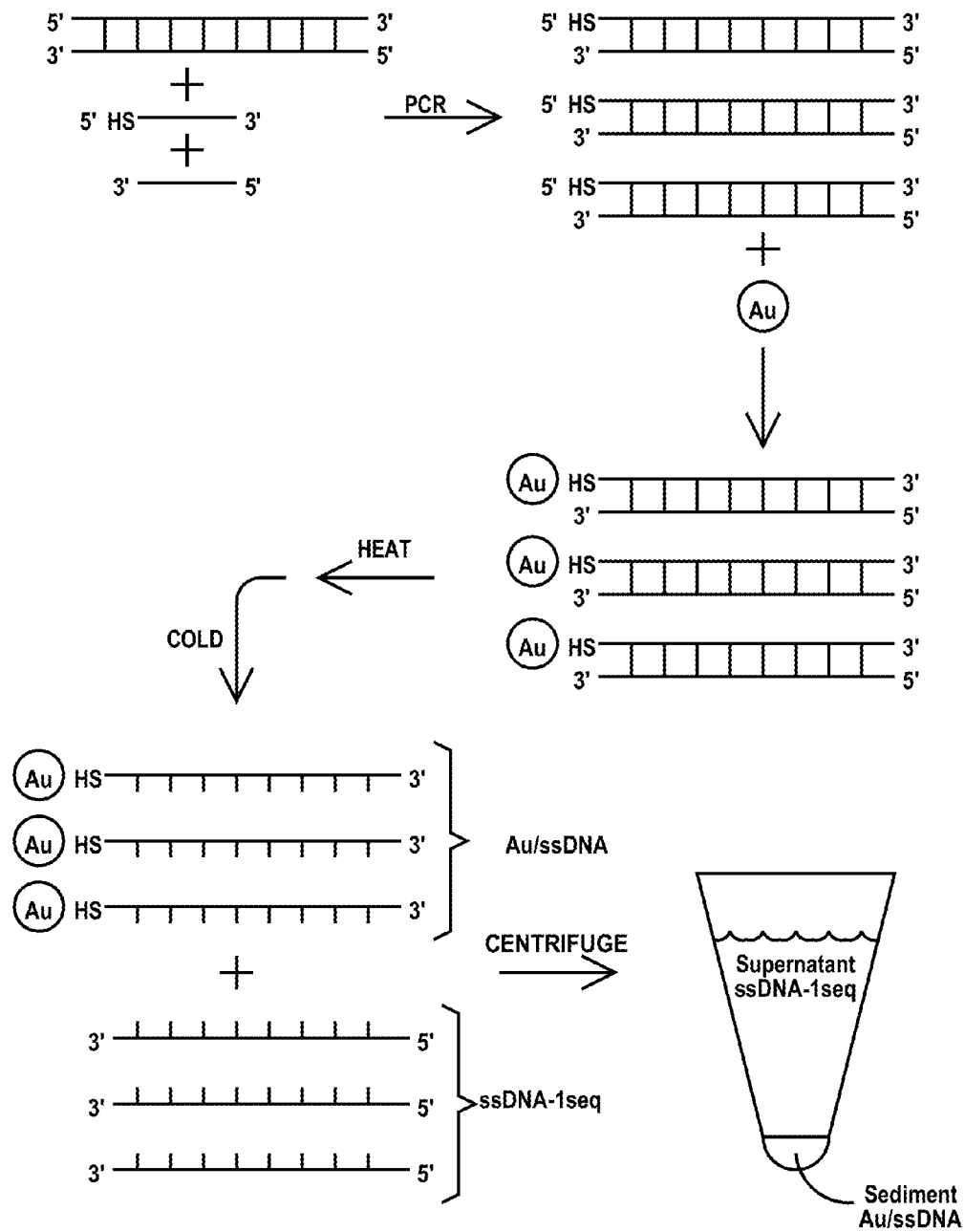
FIG. 1 is a schematic representation of the preparation of single-stranded DNA and single-wall CNT/single-stranded DNA complexes according to embodiments of the present invention.

FIG. 1 is a schematic representation of the preparation of single-stranded DNA and single-wall CNT/single-stranded DNA complexes according to embodiments of the present invention. In FIG. 1, the first step is to perform a polymerase chain reaction (PCR) designed to amplify a long length base pair segment of double-stranded DNA (dsDNA) (the template dsDNA) using two short base pair length primers. One of the primers is modified to include a thiol (—SH) group on its 5' end. The other primer is unmodified. The dsDNA may be prepared by digestion of a longer dsDNA using a restriction enzyme. The amplified dsDNA segments (now thiolated dsDNA) are modified from the original dsDNA segment by having thiol groups on the 5' end of one strand of the dsDNA segments.

In FIG. 1, the second step is to mix the thiolated dsDNA prepared in step 1, with phosphine-capped Au nanoparticles (about 5 to 25 nm in diameter) using an about 0.5 to about 1 molar ratio of thiolated dsDNA to Au. This binds a Au nanoparticle to the thiol groups of the thiolated dsDNA to produce Au/thiolated dsDNA complex (Au/dsDNA). The resultant mixture is centrifuged to separate the Au/dsDNA from unbound dsDNA.

In FIG. 1, the third step is to denature the Au/dsDNA into Au/thiolated ssDNA complex (Au/ssDNA) and free single-stranded DNA (ssDNA-1seq). In one example, denaturing is accomplished by heating and then quickly cooling the Au/dsDNA.

In FIG. 1, the fourth step is to centrifuge the Au/ssDNA and ssDNA-1seq mixture to collect the Au/ssDNA in the sediment leaving the ssDNA-1seq in the supernatant. The supernatant can then be decanted off and lyophilized to dryness. The Au/ssDNA may later be reconstituted by mixing with water to any concentration desired. The reconstituted ssDNA-1seq solution or, alternatively, the supernatant itself may be mixed with SWNTs as described infra. The ssDNA-1seq cannot self-hybridize through complementary base pairing. The length of dsDNA and the length of ssDNA-1seq is the same. In one example, the ssDNA-1seq has an extended length of about 1.4 microns. In another example, the length the ssDNA-1seq is greater than 2,000 bp. In still another example, the length the ssDNA-1seq is between about 3,000 bp and about 50,000 bp. In another example, the ssDNA-1seq has a linearly extended length greater than 1 micron.

To form single-stranded DNA segment/single-wall carbon nanotube complexes (ssDNA/SWNT), ssDNA-1seq solutions are mixed with SWNTs and sonicated (energy supplied by sound waves) at low temperatures to prevent overheating (in one example, about 4° C.) which are kept in solution by the ssNDA-1seq while un-complexed SWNT will not remain suspended and can be removed by centrifuging. In one example, about 90% of the SWNTs are complexed.

Atomic force microscopy (AFM) indicates the ssDNA/SWNT complex comprises an ssDNA strand helically wound around a SWNT. In one example, the ssDNA wrapped SWNTs had diameters between about 0.5 nanometer and about 2.0 nanometers and lengths between about 0.7 microns and about 2.0 microns. Atomic force microscopy (AFM) also indicates that on any particular SWNT the pitch of the ssDNA wrapping is constant, in one example about 60 nm, but from SWNT to SWNT the pitch could vary. In one example the pitch of the ssDNA wrapping on any particular SWNT is a constant between about 12 nm and about 80 nm.

Applicants have found that when a dsDNA segment is used to generate a ssDNA-1seq using the methods described supra and an identical dsDNA segment is used to generate an ssDNA-2seq (by conventional denaturing methods) having complementary ssDNA strands, the ssDNA-2seq will not complex SWNTs. See FIG. 3A and description infra. Further, the random sequence of bases (random because it was genomic) of the dsDNA used is in direct contradiction to current theories that an ssDNA with non-random base sequences is required to complex SWNTs, that ssDNA complexing of SWNTs involves reconciliation of specific CNT structures, that ssDNA complexing of SWNTs occurs only with ssDNA having lengths under 2,000 bp or that the tight helix formation around CNTs is ssDNA base pair sequence dependent.

Figure 3A:
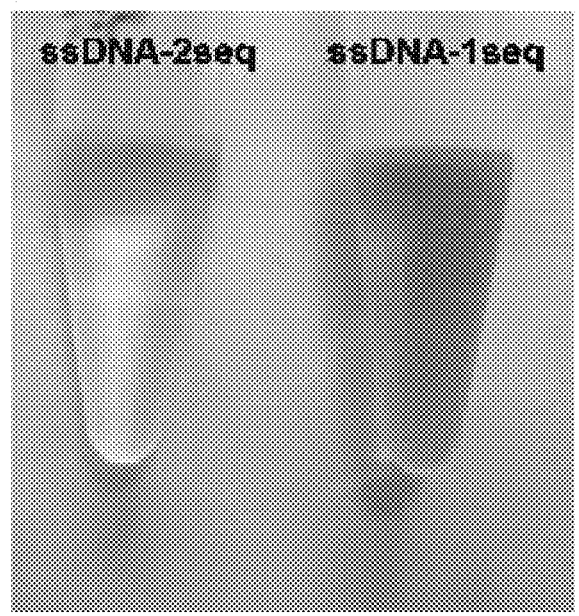
FIG. 3A is a photographic comparison of single-stranded DNA-1seq mixed with single-wall carbon nanotubes and complementary single-stranded DNA-2seq mixed with SWNTs.

FIG. 3A is a photographic comparison of ssDNA-1seq mixed with SWNTs and complementary ssDNA-2seq mixed with SWNTs. The tube labeled ssDNA-seq2 is clear indicating no reaction of ssDNA-seq2 with the SWNTs, while the tube labeled ssDNA-seq1 is dark indicating binding of ssDNA-seq1 with the SWNTs.

High density arrays of ssDNA/SWNT can be produced by air-drying droplets of ssDNA/SWNT solution on aminopropyltriethoxysilane (APTES) terminated silicon substrates which would be useful in microelectronic or nanoelectronic applications.

EXPERIMENTAL

Materials

Lambda DNA was purchased from Invitrogen, Carlsbad, Calif.

NdeI enzyme was purchased from New England Biolabs, Ipswich, Mass.

All DNA primers were purchased from Integrated DNA Technologies, Coralville, Iowa.

HiPCo carbon nanotubes were purchased from Carbon Nanotechnologies.

(bis)p-sulfonatophenyl)phenylphosphine dihydrate, dipotassium salt was purchased from Strem Chemical, Newburyport, Mass.

Sodium citrate capped Au nanoparticles were purchased from Ted Pella, Redding, Calif.

Phosphine capped Au nanoparticles were prepared by "ligand exchange" by mixing 30 mg of (bis)p-sulfonatophenyl)phenylphosphine dihydrate, dipotassium salt with a 100 ml suspension of sodium citrate capped Au nanoparticles and stirring overnight. Phosphine capped Au nanoparticles were collected by adding sodium chloride to the suspension to precipitate the phosphine capped Au nanoparticles. The phosphine capped Au nanoparticles were then re-suspended in deionized water.

Preparation of 5' Thiolated dsDNA

Template dsDNA was prepared by digesting lambda DNA with the restriction enzyme NdeI and collecting the 3796 bp lambda DNA segments. To 1 µg/100 µl PCR reactants of the 3796 bp lambda DNA segments 100 nM of a first (thiolated) primer having the sequence (SEQ ID No. 1): 5'-SH-TGCA-GATACTCACCTGCATCCTGAACCCATTGACCTC-CAACCCCGTAATA-3'. and 100 nM of a second (non-thiolated) primer having the sequence (SEQ ID No. 2): 5'-TGGTGTTGTGTGTGAGTTCGACTGGAATGATG-GAAATGGTCAGGAAGGAT-3'.

100 nM were added. Touchdown PCR was performed with 40 cycles at 95° for 30 seconds, 60° C. for 45 seconds and 72° C. for 5 minutes to generate thiolated lambda DNA having a length of 3796 bp.

Figure 2A:
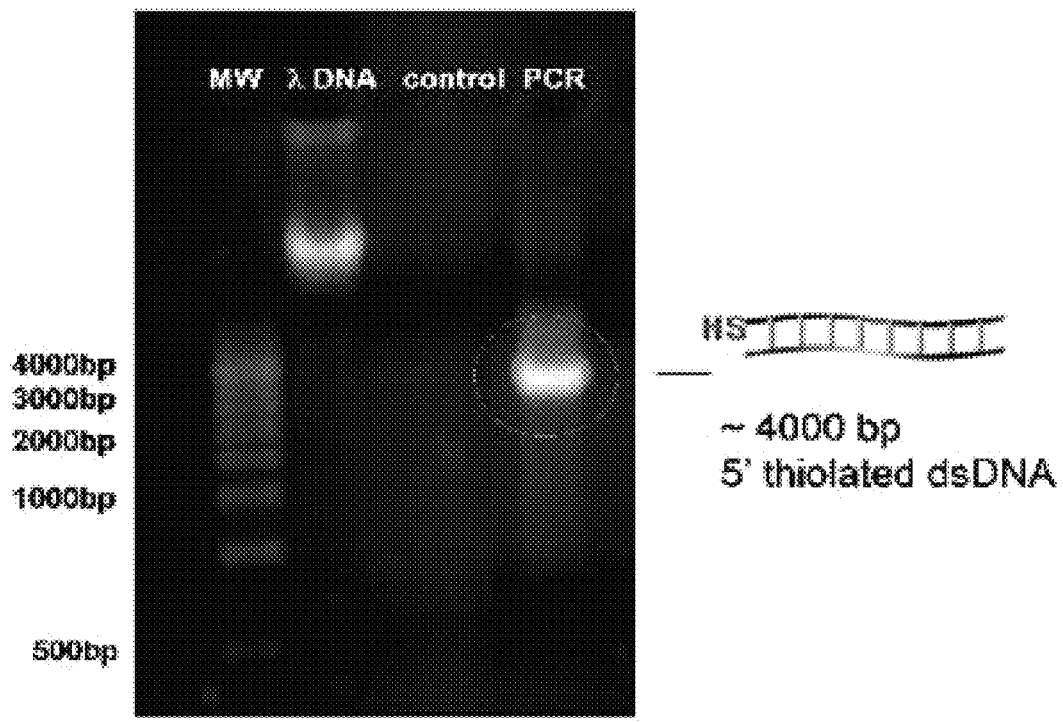
FIG. 2A is a photograph of a gel electrophoresis analysis of a thiolated lambda DNA polymerase chain reaction amplification procedure before centrifuging.

FIG. 2A is a photograph of a gel electrophoresis analysis of the thiolated lambda DNA PCR amplification procedure just described. In FIG. 2A, the column labeled "MW" includes molecular weight markers; the column labeled "λ DNA" includes starting lambda DNA only; the column labeled "control" includes the products of a PCR using primer 1 and primer 2 only, and the column labeled "PCR" includes the result of the primers and lambda DNA PCR reaction.

Preparation of Au/dsDNA Complex

Figure 2B:
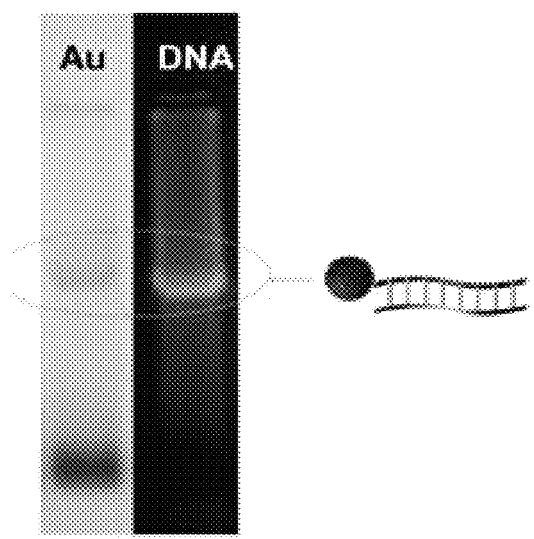
FIG. 2B is photograph of a gel electrophoresis analysis of a gold/double-stranded DNA preparation procedure.

The thiolated lambda dsDNA prepared supra, was mixed with phosphine-capped 15 nm gold particles using several different 0.5 to 1 molar ratios of thiolated dsDNA to Au nanoparticles. Typically, after 1 hour, the mixture was centrifuged, unbound thiolated dsDNA collected in the supernatant and Au/thiolated dsDNA complex (Au/dsDNA) collected in the sediment FIG. 2B is photograph of a gel electrophoresis analysis of the Au/dsDNA preparation procedure just described before centrifuging. In FIG. 2B, under white light (on the left), Au nanoparticles are seen while under UV light (on the right) ethidium bromide (EtBr) stained Au/dsDNA is seen. A Au band and the Au/dsDNA band (circled) are detected at the same distance, indicating binding of Au nanoparticles to thiolated dsDNA.

Figure 2C:
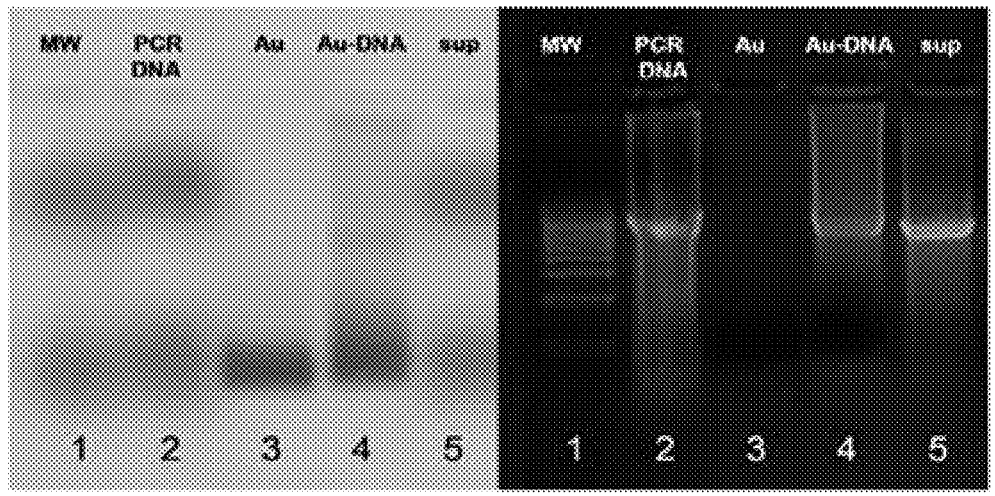
FIG. 2C is photograph of a gel electrophoresis analysis of the gold/double-stranded DNA preparation procedure after centrifuging.

FIG. 2C is photograph of a gel electrophoresis analysis of the Au/dsDNA preparation procedure just described after centrifuging. In FIG. 2C, on the left, lanes 1 through 5 are viewed under white light and on the right, lanes 1 through 5 are viewed under UV light. Lane 1 includes molecular weight markers. Lane 2 includes the 5' thiolated dsDNA which preparation was described supra. Lane 3 includes only 15 nm gold nanoparticles. Lane 4 includes re-suspended sediment containing the Au/ssDNA. Lane 5 includes the supernatant obtained after centrifugation. As is observed in lanes 4 and 5, while some of the thiolated dsDNA did indeed bind to the gold nanoparticles, a small portion of the dsDNA did not bind the gold nanoparticles.

Preparation of ssDNA

A dispersion of Au/dsDNA (from the sediment described supra in the preparation of Au/dsDNA) was thermally denatured at 98° C. and quenched on ice to produce a mixture of Au/ssDNA complex (Au/ssDNA) and unbound ssDNA. This mixture was centrifuged and the supernatant containing unbound ssDNA recovered.

ssDNA Dispersion of Carbon Nanotubes

Less than 1 mg of HiPCo nanotubes were added to 10 µg/ml solutions of the unbound ssDNA and sonicated in an ice-water bath for 10 to 20 minutes. Any insoluble material was removed after centrifugation at speeds of 400 to 1000 rpm. 10 µl droplets of ssDNA or ssDNA/SWNT solutions containing 50 mM of $MgCl_2$ were deposited on freshly cleaved mica surfaces, air dried, rinsed with water and dried under argon prior to imaging. 10 µl droplets were also deposited and dried on aminoproyltrethoxysilane (APTES) treated Si wafers but with no addition of $MgCl_2$. The APTES was deposited in a silylation oven purchased from Yield Engineering Systems, San Jose, Calif. at 150° C. for 30 minutes. All imaging was done in tapping mode in air.

Figure 3B:
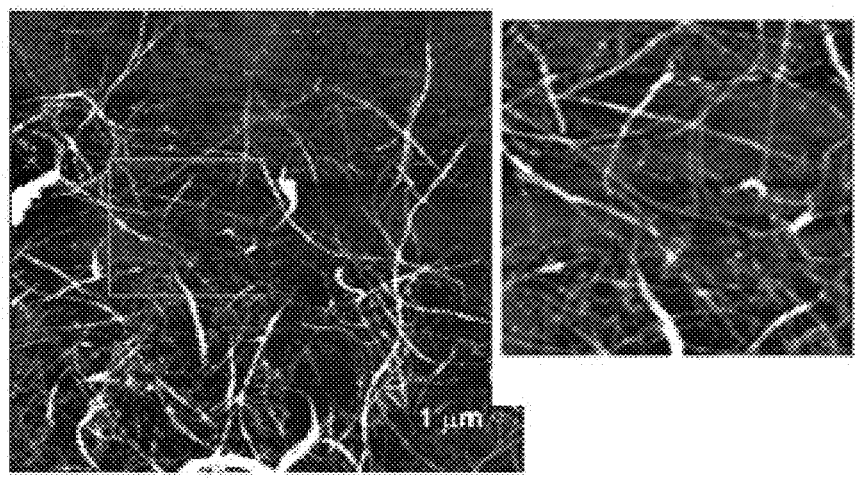
FIG. 3B is a photograph of a low magnification atomic force microscope scan of single-wall nanotube/single strand DNA complexes bound to mica.

FIG. 3B is a photograph of a low magnification atomic force microscope scan of ssDNA/SWNT prepared bound to mica. In FIG. 3B, the photograph on the left is a large area height AFM scan of ssDNA bound to SWCTs on mica. The photograph on the right is a close-up of large area scan of the left.

Figure 3C:
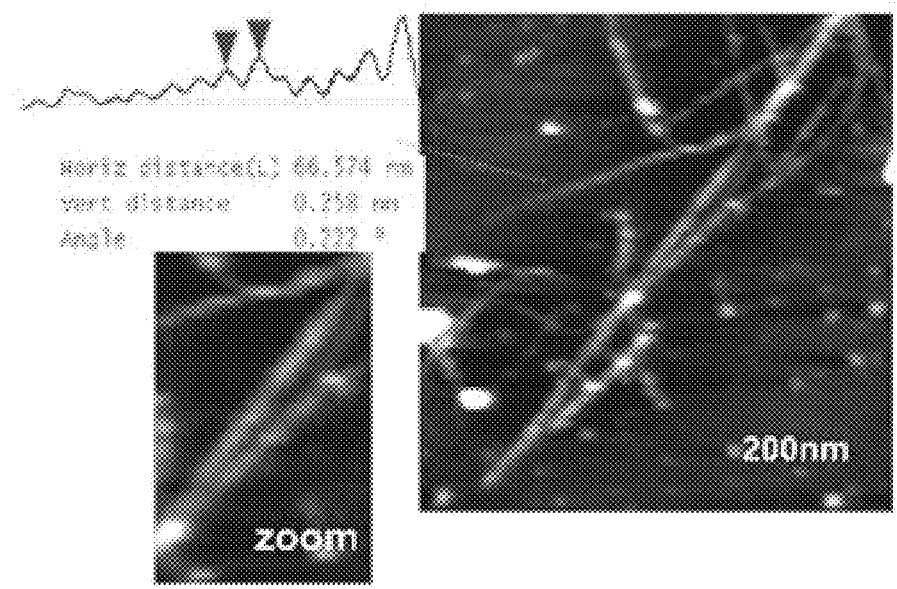
FIGS. 3C, 3D and 3E are photographs of high magnification atomic force microscope scans of single-wall nanotube/single strand DNA complexes bound to mica.
Figure 3D:
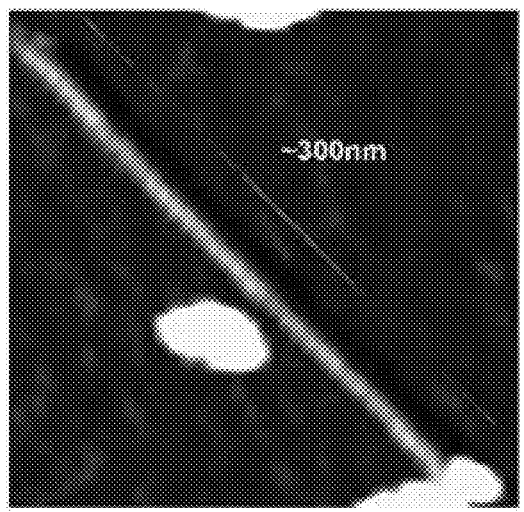
Figure 3E:
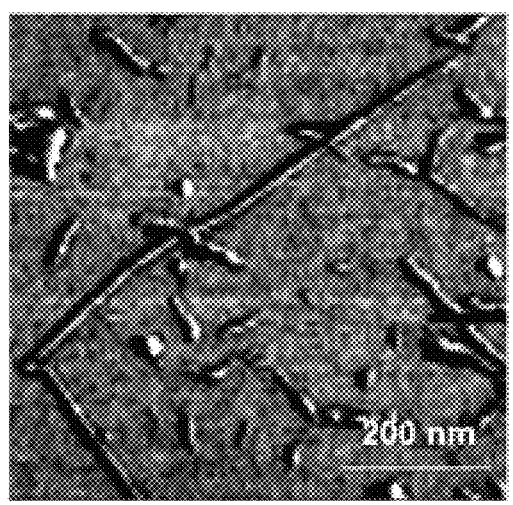

FIGS. 3C, 3D and 3E are photographs of high magnification atomic force microscope scans of ssDNA/SWNT complexes bound to mica. In FIG. 3C, on the right is a low magnification image of ssDNA/SWNTs. On the left is a height AFM image of one particular ssDNA/SWNT and above the left image is a section analysis of the one particular ssDNA/SWNT indicated by the arrows. Section analysis gives a ssDNA wrapping pitch of about 60 nm for that one particular ssDNA/SWNT. The difference in pitch should be noted in the particular structure shown in the center of the right hand image and in the left hand zoomed image. In FIG. 3D, a single ssDNA/SWNT is shown and the helically wrapping is clearly shown. In FIG. 3E, several ssDNA/SWNTs are shown. Again the helical wrapping is clearly shown.

Thus, the present invention provides DNA based methods to disperse single-wall carbon nanotubes without the limitations of specific repeating base sequences.

The description of the embodiments of the present invention is given above for the understanding of the present invention. It will be understood that the invention is not limited to the particular embodiments described herein, but is capable of various modifications, rearrangements and substitutions as will now become apparent to those skilled in the art without departing from the scope of the invention. Therefore, it is intended that the following claims cover all such modifications and changes as fall within the true spirit and scope of the invention.

What is claimed is:

1. A structure, comprising:
a single-wall carbon nanotube; and
a single-stranded genomic DNA segment helically wound around said single-wall carbon nanotube, said single-stranded DNA segment being greater than 2,000 bases in length.

2. The structure of claim 1 wherein,
said single-wall carbon nanotube has a diameter of between about 0.5 nanometer and about 2.0 nanometers and a length between about 0.7 microns and about 2.0 microns; and
said single-stranded DNA segment is a base sequence of a naturally occurring DNA molecule.

3. The structure of claim 1, wherein said single-stranded DNA segment has a length of between about 3,000 and about 50,000 bases.

4. The structure of claim 1, wherein said single-stranded DNA segment is a base sequence of bacteriophage lambda DNA.

5. The structure of claim 1, wherein said single-stranded DNA segment would have a length greater than 1 micron if it were linearly extended.

6. The structure of claim 1, further including:
a substrate;
a single-stranded DNA segment/single-wall carbon nanotube complex comprising said single-stranded DNA segment helically wound around said single-wall carbon nanotube, said single-stranded DNA segment/single-wall carbon nanotube complex bound to said substrate.

7. The structure of claim 1, wherein single-wall carbon nanotube is doped with an element selected from the group consisting of phosphorous, arsenic, boron and metals.

8. The structure of claim 1, wherein said single-stranded DNA segment has a wrapping pitch of about 60 nm.

9. A structure, comprising:
two or more single-wall carbon nanotubes; and
a corresponding single-stranded genomic DNA segment helically wound around a respective single-wall carbon nanotube, said single-stranded DNA segments being greater than 2,000 bases in length.

10. The structure of claim 9 wherein,
said single-wall carbon nanotubes have a diameter of between about 0.5 nanometer and about 2.0 nanometers and a length between about 0.7 microns and about 2.0 microns; and
each corresponding single-stranded DNA segments is a base sequence of a naturally occurring DNA molecule.

11. The structure of claim 9, wherein each corresponding single-stranded DNA segment has a length of between about 3,000 and about 50,000 bases.

12. The structure of claim 9, wherein each corresponding single-stranded DNA segments is a base sequence of bacteriophage lambda DNA.

13. The structure of claim 9, wherein each corresponding single-stranded DNA segment would have a length greater than 1 micron if they were linearly extended.

14. The structure of claim 9, wherein each of said two or more single-stranded DNA segments has an identical random base sequence.

15. The structure of claim 9, wherein each of said two or more single-stranded DNA segments has an identical base length.

16. The structure of claim 9, further including:
a substrate;
two or more single-stranded DNA segment/single-wall carbon nanotube complexes, each single-stranded DNA segment/single-wall carbon nanotube complex comprising a respective single-stranded DNA segment helically wound around a respective single-wall carbon nanotube, each single-stranded DNA segment/single-wall carbon nanotube complexes bound to said substrate.

17. The structure of claim 16, wherein said two or more single-stranded DNA segment/single-wall carbon nanotube complexes are orientated substantially in a same direction relative to a top surface of said substrate.

18. The structure of claim 9, wherein said two or more single-wall carbon nanotubes are doped with an element selected from the group consisting of phosphorous, arsenic, boron and metals.

19. The structure of claim 9, wherein said corresponding single-stranded DNA segments have a wrapping pitch of about 60 nm.

20. A method, comprising:
helically wrapping a single-stranded genomic DNA segment around a single-wall carbon nanotube, said single-stranded DNA segment being greater than 2,000 bases in length.

* * * * *

SEQUENCE LISTING

```
<160> NUMBER OF SEQ ID NOS: 2

<210> SEQ ID NO 1
<211> LENGTH: 50
<212> TYPE: DNA
<213> ORGANISM: Unknown
<220> FEATURE:
<223> OTHER INFORMATION: Suspected Synthetic, Purchased from Integrated
      DNA Technologies, Coralville, IA, USA

<400> SEQUENCE: 1
tgcagatact   cacctgcatc   ctgaacccat   tgacctccaa   ccccgtaata           50

<210> SEQ ID NO 2
<211> LENGTH: 50
<212> TYPE: DNA
<213> ORGANISM: Unknown
```

-continued

```
<220> FEATURE:
<223> OTHER INFORMATION: Suspected Synthetic, Purchased from Integrated
      DNA Technologies, Coralville, IA, USA

<400> SEQUENCE: 2
tggtgttgtg    tgtgagttcg    actggaatga    tggaaatggt    caggaaggat           50
```